US010258583B2

(12) United States Patent
Singh et al.

(10) Patent No.: US 10,258,583 B2
(45) Date of Patent: *Apr. 16, 2019

(54) EXTENDED RELEASE LIQUID COMPOSITIONS OF GUANFACINE

(71) Applicant: SUN PHARMACEUTICAL INDUSTRIES LIMITED, Mumbai, Maharashtra (IN)

(72) Inventors: Romi Barat Singh, Benares (IN); Kalaiselvan Ramaraju, Tirchirapalli (IN); Balaram Mondal, East Midnapore (IN); Ashish Kumar, Jhajjar (IN); Suchitra Kaushik, Haridwar (IN)

(73) Assignee: Sun Pharmaceutical Industries Limited, Mumbai (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/148,131

(22) Filed: May 6, 2016

(65) Prior Publication Data

US 2016/0346233 A1 Dec. 1, 2016

Related U.S. Application Data

(63) Continuation-in-part of application No. 15/133,826, filed on Apr. 20, 2016, which is a continuation of application No. PCT/IB2015/053209, filed on May 1, 2015.

(30) Foreign Application Priority Data

May 1, 2014 (IN) .......................... 1183/DEL/2014

(51) Int. Cl.
| | |
|---|---|
| A61K 9/00 | (2006.01) |
| A61K 9/10 | (2006.01) |
| A61K 9/14 | (2006.01) |
| A61K 9/50 | (2006.01) |
| A61K 31/43 | (2006.01) |
| A61K 31/155 | (2006.01) |
| A61K 31/165 | (2006.01) |
| A61K 31/522 | (2006.01) |
| A61K 31/4439 | (2006.01) |

(52) U.S. Cl.
CPC .......... *A61K 31/165* (2013.01); *A61K 9/0053* (2013.01); *A61K 9/0095* (2013.01); *A61K 9/10* (2013.01); *A61K 9/145* (2013.01); *A61K 9/5026* (2013.01); *A61K 9/5042* (2013.01); *A61K 9/5047* (2013.01); *A61K 9/5078* (2013.01); *A61K 9/5084* (2013.01); *A61K 31/155* (2013.01); *A61K 31/43* (2013.01); *A61K 31/4439* (2013.01); *A61K 31/522* (2013.01)

(58) Field of Classification Search
CPC .. A61K 31/165; A61K 9/5047; A61K 9/1676; A61K 9/1652
See application file for complete search history.

(56) References Cited

U.S. PATENT DOCUMENTS

| | | | |
|---|---|---|---|
| 3,156,369 A | 11/1964 | Bowes et al. | 215/6 |
| 3,603,469 A | 9/1971 | Magni | 215/6 |
| 3,632,645 A | 1/1972 | Bream et al. | 260/558 |
| 3,687,076 A | 8/1972 | Friant et al. | |
| 3,840,136 A | 10/1974 | Lanfranconi et al. | 215/6 |
| 3,917,063 A | 11/1975 | Chibret et al. | |
| 4,024,952 A | 5/1977 | Leitz | |
| 4,982,875 A | 1/1991 | Pozzi et al. | 222/83 |
| 5,058,770 A | 10/1991 | Herold et al. | 222/80 |
| 5,170,888 A | 12/1992 | Goncalves | |
| 5,273,760 A | 12/1993 | Oshlack et al. | 424/480 |
| 5,419,445 A | 5/1995 | Kaesemeyer | 215/11.1 |
| 5,431,915 A | 7/1995 | Harvey et al. | 424/439 |
| 5,460,828 A | 10/1995 | Santus et al. | |
| 5,472,712 A | 12/1995 | Oshlack et al. | 424/480 |
| 5,854,290 A | 12/1998 | Arnsten et al. | 514/617 |
| 5,955,106 A | 9/1999 | Moeckel et al. | |
| 6,146,996 A | 11/2000 | Morini | 206/222 |
| 6,156,340 A | 12/2000 | Adeyeye et al. | 424/463 |
| 6,287,599 B1 | 9/2001 | Burnside et al. | 424/468 |
| 6,676,966 B1 | 1/2004 | Odidi et al. | 424/464 |
| 6,811,794 B2 | 11/2004 | Burnside et al. | 424/468 |
| 6,890,957 B2 | 5/2005 | Chandran et al. | 514/634 |
| 7,214,387 B2 | 5/2007 | Sanghvi et al. | 424/468 |
| 7,748,550 B2 | 7/2010 | Cho | |
| 7,906,145 B2 | 3/2011 | Castan et al. | 424/489 |
| 8,002,734 B2 | 8/2011 | Bassarab et al. | 604/82 |
| 8,197,850 B2 | 6/2012 | Castan et al. | 424/489 |
| 8,297,456 B1 | 10/2012 | Anderson | 215/227 |
| 8,318,210 B2 | 11/2012 | Tengler et al. | 424/501 |
| 8,453,833 B2 | 6/2013 | Porter | |
| 8,491,935 B2 | 7/2013 | Mehta et al. | 424/487 |
| 8,541,018 B2 | 9/2013 | Radke et al. | 424/439 |

(Continued)

FOREIGN PATENT DOCUMENTS

| | | | | |
|---|---|---|---|---|
| CH | 567978 | | 8/1975 | |
| EP | 0601508 A2 | * | 6/1994 | ........... A61K 9/0095 |

(Continued)

OTHER PUBLICATIONS

Intuiv : Highlights of prescribing information (201X Shire US Inc, Revised Feb. 2013).*

(Continued)

Primary Examiner — Gina C Justice
(74) Attorney, Agent, or Firm — Stanley Liang; Liang, Frank LLP

(57) ABSTRACT

The present invention relates to extended release liquid compositions of guanfacine. The extended release liquid compositions of the present invention are bioequivalent to marketed extended release tablet compositions of guanfacine. Said extended release liquid compositions provide substantially similar in-vitro dissolution release profile upon storage for at least seven days. Further, the extended release liquid compositions are stable. The extended release liquid compositions are in the form of ready-to-use liquid compositions or reconstituted liquid compositions. It also relates to processes for the preparation of said extended release liquid compositions.

18 Claims, No Drawings

(56) References Cited

U.S. PATENT DOCUMENTS

| | | |
|---|---|---|
| 8,960,424 B1 | 2/2015 | Anderson |
| 9,132,950 B1 | 9/2015 | Anderson et al. |
| 2001/0032643 A1 | 10/2001 | Hochrainer et al. ..... 128/200.21 |
| 2003/0171407 A1 | 9/2003 | Freese et al. ................. 514/342 |
| 2003/0199846 A1 | 10/2003 | Fowles et al. ................. 604/403 |
| 2004/0062800 A1 | 4/2004 | Burnside et al. ............. 424/468 |
| 2004/0062802 A1 | 4/2004 | Hermelin ...................... 424/468 |
| 2004/0109891 A1 | 6/2004 | Sanghvi et al. ............. 424/468 |
| 2005/0279653 A1 | 12/2005 | Williams-Lucas et al. |
| 2007/0193894 A1 | 8/2007 | Macken et al. ............... 206/219 |
| 2008/0008765 A1 | 1/2008 | Schwarz et al. .............. 424/493 |
| 2008/0095855 A1 | 4/2008 | Schwarz |
| 2008/0118570 A1 | 5/2008 | Liu et al. ...................... 424/490 |
| 2008/0124432 A1 | 5/2008 | Ma |
| 2008/0202950 A1 | 8/2008 | Anderson ..................... 206/219 |
| 2008/0314775 A1 | 12/2008 | Owoc |
| 2009/0123538 A1 | 5/2009 | Alani et al. .................... 424/464 |
| 2009/0142378 A1 | 6/2009 | Frisbee ......................... 424/400 |
| 2009/0176691 A1 | 7/2009 | Bennis et al. .................... 514/3 |
| 2009/0325938 A1 | 12/2009 | Lichter et al. ................ 514/220 |
| 2010/0092562 A1 | 4/2010 | Hollenbeck et al. ......... 424/488 |
| 2010/0282624 A1 | 11/2010 | Paganuzzi |
| 2010/0330150 A1 | 12/2010 | Venkatesh et al. ........... 424/439 |
| 2011/0268808 A1 | 11/2011 | Jain et al. |
| 2011/0313046 A1 | 12/2011 | Ermer ........................... 514/617 |
| 2012/0178666 A1 | 7/2012 | Franklin et al. ................ 514/1.3 |
| 2012/0220930 A1 | 8/2012 | Griffiths et al. ............... 604/89 |
| 2013/0109659 A1 | 5/2013 | Soler Ranzani et al. ..... 514/158 |
| 2014/0050796 A1* | 2/2014 | Tengler ................ A61K 9/0056 424/494 |
| 2014/0309271 A1 | 10/2014 | Price |
| 2014/0319141 A1 | 10/2014 | Stratis et al. .................. 220/277 |
| 2015/0021214 A1 | 1/2015 | Besic et al. |
| 2016/0228360 A1 | 8/2016 | Kumar et al. |
| 2016/0228379 A1 | 8/2016 | Kumar et al. |
| 2016/0271070 A1 | 9/2016 | Singh et al. |
| 2016/0317388 A1 | 11/2016 | Bhargava et al. |
| 2016/0346233 A1 | 12/2016 | Singh et al. |
| 2016/0346235 A1 | 12/2016 | Singh et al. |
| 2017/0119627 A1 | 1/2017 | Gambino et al. |
| 2017/0216142 A1 | 8/2017 | Mittal et al. |
| 2017/0304234 A1 | 10/2017 | Singh et al. |
| 2017/0312177 A1 | 11/2017 | Bhargava et al. |
| 2018/0133399 A1 | 5/2018 | Kumar et al. |
| 2018/0221290 A1 | 8/2018 | Singh et al. |
| 2018/0221314 A1 | 8/2018 | Singh et al. |

FOREIGN PATENT DOCUMENTS

| | | | |
|---|---|---|---|
| EP | 1122186 A1 | 8/2001 | |
| EP | 1 140 027 | 10/2005 | ............... A61K 9/16 |
| FR | 2897267 A1 * | 8/2007 | ........... A61K 9/0095 |
| FR | 2 897 267 B1 | 2/2016 | |
| JP | 2012/514632 | 6/2012 | |
| WO | WO 00/38655 | 7/2000 | ............... A61K 9/16 |
| WO | WO 2006/030297 | 3/2003 | ............... A61K 9/16 |
| WO | WO 2004/012715 A1 | 2/2004 | |
| WO | WO 2005/097040 A1 | 10/2005 | |
| WO | WO 2006/086856 A1 | 8/2006 | |
| WO | WO 2008/122993 | 10/2008 | ............... A61K 9/16 |
| WO | WO 2010/045656 A3 | 4/2010 | |
| WO | WO 2011/077451 | 6/2011 | ............... A61K 9/28 |
| WO | WO 2011/107855 | 9/2011 | ............... A61K 9/50 |
| WO | WO 2011/150506 | 12/2011 | ............... A61K 9/48 |
| WO | WO 2012052853 A3 | 4/2012 | |
| WO | WO 2012/063257 | 5/2012 | ............. A61K 47/30 |
| WO | WO 2013043064 A1 | 3/2013 | |
| WO | WO 2013091882 A1 | 6/2013 | |
| WO | WO 2014/174119 | 10/2014 | ........... A61K 31/155 |
| WO | WO 2015166472 A1 | 11/2015 | |
| WO | WO 2015166473 A1 | 11/2015 | |
| WO | WO 2016178130 A1 | 11/2016 | |
| WO | WO 2016178131 A1 | 11/2016 | |
| WO | WO 2016178132 A1 | 11/2016 | |
| WO | WO 2017182851 A1 | 10/2017 | |
| WO | WO 2017182852 A1 | 10/2017 | |
| WO | WO 2017191485 A1 | 11/2017 | |

OTHER PUBLICATIONS

Kristine, "EKG Results/Tenex", Dr. Mom's Spot (Mar. 26, 2010) Available: http://drmomsspot.blogspot.com/2010/03/ekg-results-tenex.html.

Co-pending PCT Application No. PCT/IB2015/053209 filed May 1, 2015.

International Search Report and Written Opinion for International Application No. PCT/IB2015/053209, issued by PCT dated Aug. 14, 2015.

International Preliminary Report on Patentability for International Application No. PCT/IB2015/053209, issued by PCT dated Nov. 10, 2016.

Co-pending U.S. Appl. No. 15/133,826, filed Apr. 20, 2016.

Office Action for U.S. Appl. No. 15/133,826, issued by USPTO dated Jul. 28, 2016.

Co-pending PCT Application No. PCT/IB2016/052604 filed May 6, 2016.

International Search Report and Written Opinion for International Application No. PCT/IB2016/052604, issued by PCT dated Aug. 31, 2016.

Co-pending U.S. Appl. No. 15/148,069, filed May 6, 2016.

Office Action for U.S. Appl. No. 15/148,069, issued by USPTO dated Nov. 2, 2016.

Co-pending PCT Application No. PCT/IB2016/052607 filed May 6, 2016.

International Search Report and Written Opinion for International Application No. PCT/IB2016/052607, issued by PCT dated Sep. 2, 2016.

Co-pending PCT Application No. PCT/IB2016/052485 filed May 2, 2016.

International Search Report and Written Opinion for International Application No. PCT/IB2016/052485, issued by PCT dated Aug. 31, 2016.

Co-pending U.S. Appl. No. 15/144,026, filed May 2, 2016.

Office Action for U.S. Appl. No. 15/144,026, issued by USPTO dated Oct. 12, 2016.

Co-pending PCT Application No. PCT/IB2015/055780 filed Jul. 30, 2015.

International Search Report and Written Opinion for International Application No. PCT/IB2015/055780, issued by PCT dated Dec. 7, 2015.

Co-pending PCT Application No. PCT/IB2016/052486 filed May 2, 2016.

International Search Report and Written Opinion for International Application No. PCT/IB2016/052486, issued by PCT dated Sep. 9, 2016.

Co-pending U.S. Appl. No. 15/144,058, filed May 2, 2016.

Co-pending U.S. Appl. No. 15/352,993, filed Nov. 16, 2016.

Lopez-Liuchi et al., "Therapy for type 2 diabetes: where do we stand after the UK Prospective Diabetes Study?," *European Journal of Endocrinology*, 140:4-6 (1999).

Murtaza,"Ethylcellulose Microparticles: A Review," *Drug Research*, 69(1):11-22 (2012).

Co-pending PCT Application No. PCT/IB2015/053207 filed May 1, 2015, published as WO 2015/166472 on Nov. 5, 2015.

International Search Report and Written Opinion for International Application No. PCT/IB2015/053207, issued by US/ISA dated Aug. 7, 2015.

International Preliminary Report on Patentability for International Application No. PCT/IB2015/053207, issued by WIPO dated Mar. 16, 2016.

Co-pending U.S. Appl. No. 15/133,773, filed Apr. 20, 2016, published as U.S. 2016/0228360 on Aug. 11, 2016.

Restriction Requirement for U.S. Appl. No. 15/133,773, issued by USPTO dated Jun. 10, 2016.

Office Action for U.S. Appl. No. 15/133,773, issued by USPTO dated Jul. 27, 2016.

(56) References Cited

OTHER PUBLICATIONS

Final Office Action for U.S. Appl. No. 15/133,773, issued by USPTO dated Dec. 16, 2016.
Final Office Action for U.S. Appl. No. 15/133,773, issued by USPTO dated Apr. 13, 2017.
Co-pending PCT Application No. PCT/IB2016/052484 filed May 2, 2016, published as WO 2016/178130 on Nov. 10, 2016.
International Search Report and Written Opinion for International Application No. PCT/IB2016/052484, issued by US/ISA dated Sep. 8, 2016.
Co-pending U.S. Appl. No. 15/144,000, filed May 2, 2016, not yet published.
Office Action for U.S. Appl. No. 15/144,000, issued by USPTO dated Jun. 23, 2016.
Final Office Action for U.S. Appl. No. 15/144,000, issued by USPTO dated Nov. 4, 2016.
Office Action for U.S. Appl. No. 15/144,000, issued by USPTO dated Feb. 14, 2017.
Restricted Requirement for U.S. Appl. No. 15/133,826, issued by USPTO dated Jun. 23, 2016.
Final Office Action for U.S. Appl. No. 15/133,826, issued by USPTO dated Dec. 20, 2016.
Office Action for U.S. Appl. No. 15/133,826, issued by USPTO dated Feb. 14, 2017.
Restriction Requirement for U.S. Appl. No. 15/148,069, issued by USPTO dated Jul. 21, 2016.
Final Office Action for U.S. Appl. No. 15/148,069, issued by USPTO dated Mar. 20, 2017.
Final Office Action for U.S. Appl. No. 15/144,026, issued by USPTO dated Apr. 6, 2017.
International Preliminary Report on Patentability for International Application No. PCT/IB2015/055780, issued by WIPO dated Feb. 9, 2017.
Co-pending U.S. Appl. No. 15/329,070, filed Jan. 25, 2017, not yet published.
Restriction Requirement for U.S. Appl. No. 15/144,058, issued by USPTO dated Sep. 30, 2016.
Office Action for U.S. Appl. No. 15/144,058, issued by USPTO dated Dec. 16, 2016.
Office Action for U.S. Appl. No. 15/144,058, issued by USPTO dated May 11, 2017.
Office Action for U.S. Appl. No. 15/352,993, issued by USPTO dated Mar. 24, 2017.
Co-pending PCT Application No. PCT/IB2016/052488 filed May 2, 2016, not yet published.
International Search Report and Written Opinion for International Application No. PCT/IB2016/052488, issued by US/ISA dated Aug. 31, 2016.
Co-pending U.S. Appl. No. 15/144,098, filed May 2, 2016, not yet published.
Steeman, 2009. Innovative dispensing bottle caps for sensitive vitamins [online]. Best in Packaging. Available from: http://bestinpackaging.com/2009/05/29/innovative-dispensing-bottle-caps-for-sensitive-vitamins/.
Medela Breast Milk Bottle Set, Target, published on or before 2010. Available from: www.target.com/p/medela-breast-milk-set-8oz-3ct/-/A-11189915 (Accessed on: Aug. 14, 2017).
Final Office Action for U.S. Appl. No. 15/144,058, issued by USPTO dated Jul. 21, 2017.
Office Action for U.S. Appl. No. 15/144,098, issued by USPTO dated Jul. 13, 2017.
Office Action for U.S. Appl. No. 15/133,773, issued by USPTO dated Aug. 1, 2017.
Office Action for U.S. Appl. No. 15/148,069, issued by USPTO dated Aug. 10, 2017.
Office Action for U.S. Appl. No. 15/144,026, issued by USPTO dated Aug. 24, 2017.

Office Action for U.S. Appl. No. 15/352,993, issued by USPTO dated Aug. 24, 2017.
Final Office Action for U.S. Appl. No. 15/144,000, issued by USPTO dated Aug. 24, 2017.
Continuation U.S. Appl. No. 15/800,682, filed Nov. 1, 2017, not yet published.
Office Action for U.S. Appl. No. 15/329,070, issued by USPTO dated Nov. 21, 2017.
International Preliminary Report on Patentability for International Application No. PCT/IB2016/052485, issued by WIPO dated Nov. 16, 2017.
International Preliminary Report on Patentability for International Application No. PCT/IB2016/052484, issued by WIPO dated Nov. 16, 2017.
International Preliminary Report on Patentability for International Application No. PCT/IB2016/052486, issued by WIPO dated Nov. 16, 2017.
Final Office Action for U.S. Appl. No. 15/133,773, issued by USPTO dated Dec. 11, 2017.
Restriction Requirement for U.S. Appl. No. 15/800,682, issued by USPTO dated Dec. 15, 2017.
Office Action for U.S. Appl. No. 15/144,058, issued by USPTO dated Jan. 16, 2018.
U.S. Appl. No. 15/853,219, filed Dec. 22, 2017, not yet published.
Final Office Action for U.S. Appl. No. 15/148,069, issued by USPTO dated Jan. 19, 2018.
Final Office Action for U.S. Appl. No. 15/352,993, issued by USPTO dated Feb. 8, 2018.
Final Office Action for U.S. Appl. No. 15/144,026, issued by USPTO dated Feb. 7, 2018.
Final Office Action for U.S. Appl. No. 15/133,826, issued by USPTO dated Feb. 12, 2018.
Final Office Action for U.S. Appl. No. 15/144,098, issued by USPTO dated Feb. 22, 2018.
U.S. Appl. No. 15/942,711, filed Apr. 2, 2018, not yet published.
U.S. Appl. No. 15/942,840, filed Apr. 2, 2018, not yet published.
Timmins et al, "Steady-State Pharmacokinet of a Novel Extended-Release Metformin Formulation", Clinical Pharmacokinet., 44(7):721-729 (2005).
Office Action for U.S. Appl. No. 15/133,773, issued by USPTO dated May 18, 2018.
Office Action for U.S. Appl. No. 15/942,840, issued by USPTO dated May 29, 2018.
EP Extended Search Report dated Feb. 16, 2018 for European Patent Application No. 15827750.9.
Office Action for AU Application No. 2017279809, issued by AU PTO dated Jun. 1, 2018.
Office Action for AU Application No. 2017254908, issued by AU PTO dated Jun. 1, 2018.
Final Office Action for U.S. Appl. No. 15/329,070, issued by USPTO dated Jun. 11, 2018.
Office Action for U.S. Appl. No. 15/942,711, issued by USPTO dated Jun. 20, 2018.
European Extended Search Report dated Jun. 6, 2018 for European Patent Application No. 17210326.9.
Office Action for U.S. Appl. No. 15/329,070, issued by USPTO dated Aug. 30, 2018.
Office Action for U.S. Appl. No. 15/144,000, issued by USPTO dated Aug. 31, 2018.
Office Action for U.S. Appl. No. 15/800,682, issued by USPTO dated Apr. 10, 2018.
Office Action for U.S. Appl. No. 15/144,098, issued by USPTO dated Sep. 7, 2018.
Final office action dated Sep. 6, 2018 for U.S. Appl. No. 15/853,219.
Office action dated Dec. 11, 2018 for JP Application No. 2017-508782.
EESR dated Nov. 9, 2018 for EP Application No. 16789381.7.

\* cited by examiner

EXTENDED RELEASE LIQUID COMPOSITIONS OF GUANFACINE

FIELD OF THE INVENTION

The present invention relates to extended release liquid compositions of guanfacine. The extended release liquid compositions of the present invention are bioequivalent to marketed extended release tablet compositions of guanfacine. Said extended release liquid compositions provide substantially similar in-vitro dissolution release profile upon storage for at least seven days. Further, the extended release liquid compositions are stable. The extended release liquid compositions are in the form of ready-to-use liquid compositions or reconstituted liquid compositions. It also relates to processes for the preparation of said extended release liquid compositions.

BACKGROUND OF THE INVENTION

Guanfacine is a central alpha$_{2A}$-adrenergic receptor agonist indicated for the treatment of Attention Deficit Hyperactivity Disorder (ADHD) as a monotherapy and as an adjunctive therapy to stimulant medications. Guanfacine hydrochloride, a pharmaceutically acceptable salt of guanfacine, is a white to off-white crystalline powder, sparingly soluble in water (approximately 1 mg/mL) and alcohol and slightly soluble in acetone. The chemical designation for guanfacine hydrochloride is N-amidino-2-(2,6-dichlorophenyl)-acetamide monohydrochloride. The chemical structure is:

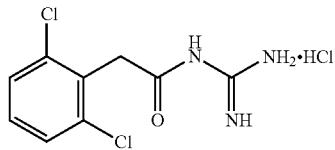

Guanfacine and its pharmaceutically acceptable salts are disclosed in U.S. Pat. No. 3,632,645. U.S. Pat. No. 5,854,290 discloses the method of treating a behavioral disinhibition (e.g. Attention-Deficit Hyperactivity Disorder) in a primate with minimal sedative side effects by administering thereto a therapeutically effective amount of guanfacine.

U.S. Pat. No.'s. 6,287,599 and 6,811,794 describe sustained release tablet compositions of guanfacine, comprising at least one non-pH dependent sustained release agent, and at least one pH dependent agent that increases the rate of release of guanfacine from the tablet at a pH in excess of 5.5.

Guanfacine is presently marketed only in solid dosage forms i.e. immediate release and extended release tablets for oral administration. However, these solid dosage forms are not suited for patients who have difficulty in swallowing. Further, solid dosage forms may not be convenient, when chronic therapy is needed.

Therefore, there exists a need in the art for liquid compositions of guanfacine for better patient compliance, convenience and dose flexibility. Of particular advantage would be extended release liquid compositions that can provide effective plasma levels over a prolonged period of time. In view of this, extended release liquid compositions are clearly advantageous over the presently available solid dosage forms.

However, it remains a great challenge to formulate an extended release liquid composition of guanfacine. First challenge is to avoid the release of guanfacine from extended release units into a liquid carrier during storage, and to release only when the composition enters the gastrointestinal tract. Guanfacine may leach out from the extended release units into the liquid carrier during storage, thus obliterating the whole objective of the extended release. Furthermore, the irregular release may lead to sub-therapeutic or toxic effects leading to serious medical conditions. Another challenge with the liquid composition of guanfacine is the stability of guanfacine, both during the manufacturing process and shelf-life.

The inventors of the present invention have addressed all these challenges and have for the first time developed extended release liquid compositions of guanfacine. The compositions described herein are capable of providing consistent in-vitro extended release of guanfacine which further ensures steady plasma concentrations throughout the shelf life of the compositions. Further, said extended release liquid compositions provide desired in-vivo release of guanfacine and are bioequivalent to a reference composition. Furthermore, the extended release liquid compositions are stable both during manufacturing and storage period.

Therefore, the present invention is a significant advance over the available solid dosage forms of guanfacine and fulfills the long felt need to improve patient compliance by providing an extended release liquid composition of guanfacine with consistent release and acceptable stability.

The extended release liquid compositions of guanfacine offer additional advantages as they are easy to manufacture with functional reproducibility. The extended release liquid compositions described herein are provided with a pleasant mouth feel thereby further enhancing patient compliance and ease of administration.

SUMMARY OF THE INVENTION

The present invention relates to extended release liquid compositions of guanfacine. The extended release liquid compositions of the present invention are bioequivalent to a marketed extended release tablet of guanfacine. Said compositions provide substantially similar in-vitro dissolution release profile upon storage for at least seven days. Further, the extended release liquid compositions of the present invention are stable.

The extended release liquid compositions are in the form of ready-to-use liquid compositions or reconstituted liquid compositions. The extended release liquid compositions offer better patient compliance and dosing flexibility based on age and body weight of the patients. It further relates to processes for the preparation of said extended release liquid compositions.

DETAILED DESCRIPTION OF THE INVENTION

A first aspect of the present invention provides an extended release liquid composition comprising guanfacine in a pharmaceutically acceptable carrier.

A second aspect of the present invention provides an extended release liquid composition comprising guanfacine in a pharmaceutically acceptable carrier, wherein the composition comprises guanfacine in a concentration from about 0.1 mg/mL to about 12.0 mg/mL of the composition.

In a particular embodiment, the composition comprises guanfacine in a concentration from about 1.0 mg/mL to about 7.0 mg/mL of the composition.

A third aspect of the present invention provides an extended release liquid composition comprising guanfacine in a pharmaceutically acceptable carrier, wherein the extended release liquid composition is bioequivalent to a marketed extended release tablet composition.

According to one embodiment, the composition exhibits an $AUC_{0 \to \infty}$ ranging from about 34000 hr*pg/mL to about 220000 hr*pg/mL upon administration of a 4 mg dose of guanfacine under fasting state. In a particular embodiment, the composition exhibits an $AUC_{0 \to \infty}$ ranging from about 34000 hr*pg/mL to about 160000 hr*pg/mL upon administration of a 4 mg dose of guanfacine under fasting state.

According to another embodiment, the composition exhibits an $AUC_{last}$ ranging from about 32000 hr*pg/mL to about 180000 hr*pg/mL upon administration of a 4 mg dose of guanfacine under fasting state. In a particular embodiment, the composition exhibits an $AUC_{last}$ ranging from about 32000 hr*pg/mL to about 150000 hr*pg/mL upon administration of a 4 mg dose of guanfacine under fasting state.

According to another embodiment, the composition exhibits a $C_{max}$ from about 1800 pg/mL to about 9000 pg/mL upon administration of a 4 mg dose of guanfacine under fasting state. In a particular embodiment, the composition exhibits a $C_{max}$ from about 1800 pg/mL to about 4000 pg/mL upon administration of a 4 mg dose of guanfacine under fasting state.

According to another embodiment, the composition exhibits a $T_{max}$ from about 2 hours to about 10 hours upon administration of a 4 mg dose of guanfacine under fasting state.

According to another embodiment, the composition exhibits a $T_{lag}$ of less than about 2 hours, upon administration of a 4 mg dose of guanfacine under fasting state.

A fourth aspect of the present invention provides an extended release liquid composition comprising guanfacine in a pharmaceutically acceptable carrier, wherein the composition is characterized by having an in-vitro dissolution release profile when determined for a 4 mg dose of 1 mg/mL concentration using USP type II apparatus at 75 rpm, in 900 mL of hydrochloric acid buffer with a pH 2.2 at 37° C. as follows:

a. not more than about 30% of guanfacine released after 1 hour;
b. about 35 to about 75% of guanfacine released after 4 hours; and
c. not less than about 75% of guanfacine released after 24 hours.

According to another embodiment, the in-vitro dissolution release profile of the composition upon storage for at least seven days remains substantially similar to the initial in-vitro dissolution release profile.

A fifth aspect of the present invention provides an extended release liquid composition comprising guanfacine in a pharmaceutically acceptable carrier, wherein the composition is a stable composition. Particularly, the composition is stable for at least seven days. More particularly, the composition is stable for at least one month, or further, to the extent necessary for the sale and use of the composition.

According to another embodiment, the composition comprises less than about 1.0% w/w of 2,6-dichlorophenyl acetic acid. Particularly, the composition comprises less than about 0.7% w/w of 2,6-dichlorophenyl acetic acid.

According to another embodiment, the composition comprises less than about 3.0% w/w of total related substances. Particularly, the composition comprises less than about 2.0% w/w of total related substances.

A sixth aspect of the present invention provides an extended release liquid composition comprising guanfacine in a pharmaceutically acceptable carrier, wherein the composition has a pH of less than about 6.8.

A seventh aspect of the present invention provides an extended release liquid composition comprising guanfacine in a pharmaceutically acceptable carrier, wherein the composition is a ready-to-use liquid composition or a reconstituted liquid composition.

According to another embodiment, the ready-to-use liquid composition comprises a suspension, a syrup, a concentrate, an elixir or an emulsion.

According to another embodiment, the reconstituted liquid composition comprises a suspension reconstituted from dry powder comprising granules, pellets, or beads.

According to another embodiment of the above aspects, the composition is a taste-masked composition.

An eighth aspect of the present invention provides an extended release liquid composition comprising guanfacine in a pharmaceutically acceptable carrier, wherein the composition comprises:

(i) cores comprising guanfacine and a release-controlling agent; and
(ii) a pharmaceutically acceptable carrier.

In one embodiment, guanfacine may be present in the core or layered over an inert particle to form a core.

According to another embodiment, the core is in the form of a bead, a pellet, a granule, a spheroid, or the like.

According to another embodiment, the inert particle is selected from a group comprising a non-pareil seed, a microcrystalline cellulose sphere, a dibasic calcium phosphate bead, a mannitol bead, a silica bead, a tartaric acid pellet, or a wax based pellet.

In another embodiment, the release-controlling agent may be present in the core or coated over the guanfacine core or both.

According to another embodiment, the release-controlling agent is selected from the group comprising a pH-dependent release controlling agent, a pH-independent release controlling agent, or mixtures thereof.

According to another embodiment, the core further comprises other pharmaceutically acceptable excipients selected from the group comprising acids, osmogents, binders, glidants, or combinations thereof.

According to another embodiment, the pharmaceutically acceptable carrier comprises one or more of liquid adjuvants and other pharmaceutically acceptable excipients.

According to another embodiment, the other pharmaceutically acceptable excipients in the carrier are selected from the group comprising acids, osmogents, buffering agents, suspending agents, glidants, sweetening agents, flavors, colorants, anti-caking agents, wetting agents, preservatives, antioxidants, chelating agents, binders, viscosity modifiers, and combinations thereof.

According to another embodiment of the above aspects, the cores comprising guanfacine and a release-controlling agent have a particle size $d_{90}$ value of less than about 1.5 mm.

According to another embodiment of the above aspects, the extended release liquid composition is characterized by having an osmolality ratio of at least about 1.

According to another embodiment of the above aspects, the pharmaceutically acceptable carrier has an osmolality of about 1 osmol/kg or more than about 1 osmol/kg of the carrier.

According to another embodiment, the composition further comprises guanfacine in an immediate release form.

A ninth aspect of the present invention, provides a method of treating Attention Deficit Hyperactivity Disorder by administering an extended release liquid composition comprising guanfacine in a pharmaceutically acceptable carrier.

In an embodiment of the above aspect, the extended release liquid composition is administered once daily.

The term "guanfacine," as used herein, refers to guanfacine, as well as its pharmaceutically acceptable salts, polymorphs, hydrates, solvates, prodrugs, chelates, and complexes. Exemplary salts include salts of inorganic or organic acids such as hydrochloride, hydrobromide, sulphate, sulfamate, nitrate, phosphate, formate, mesylate, citrate, benzoate, fumarate, maleate, tartrate, and succinate. A particularly preferred salt of guanfacine is guanfacine hydrochloride.

The extended release liquid composition comprises guanfacine in a concentration from about 0.1 mg/mL to about 12 mg/mL of the composition. Preferably, the extended release liquid composition comprises guanfacine in a concentration from about 1.0 mg/mL to about 7.0 mg/mL of the composition.

As used herein, the term "extended release," is used to define a release profile to effect delivery of guanfacine over an extended period of time, as being between about 60 minutes to about 2, 4, 6, 8, 12 or 24 hours. The extended release includes sustained release, controlled release, multiphase release, delayed release, pulsatile release, chrono release and the like.

The extended release liquid composition of the present invention is bioequivalent to a reference product. The reference product is an extended release tablet of guanfacine available in strengths of 1 mg, 2 mg, 3 mg and 4 mg marketed under the brand name Intuniv® by Shire.

The term "bioequivalent," as used herein, is a term of art and is defined to mean the term used by the drug approval agencies, such as the US Food and Drug Administration: "the absence of a significant difference in the rate and extent to which the active ingredient or active moiety in pharmaceutical equivalents or pharmaceutical alternatives becomes available at the site of drug action when administered at the same molar dose under similar conditions in an appropriately designed study." Bioequivalence of different formulations of the same drug substance involves equivalence with respect to the rate and extent of drug absorption. Two formulations whose rate and extent of absorption differ by −20%/+25% or less are generally considered to be bioequivalent. Detailed guidelines for establishing the bioequivalence of a formulation with a reference formulation have been published by the FDA Office of Generic Drugs, Division of Bioequivalence. Pharmacokinetic parameters such as $C_{max}$, $T_{max}$, $AUC_{last}$ and $AUC_{0 \to \infty}$ are used to establish bioequivalency.

The term "$AUC_{0 \to \infty}$," as used herein, refers to the area under the plasma concentration-time curve extrapolated to infinity.

The term "$AUC_{last}$," as used herein, refers to the area under the plasma concentration-time curve from time 0 up to the time corresponding to the last quantifiable concentration.

The term "$C_{max}$" as used herein refers to the maximum plasma concentration of guanfacine.

The term "$T_{max}$," as used herein, refers to the time to reach maximum plasma guanfacine concentration of guanfacine.

The term "Lag time ($T_{lag}$)," as used herein, refers to the time between administration of the composition and the first quantifiable plasma level concentration of guanfacine in the plasma concentration versus time curve.

In the context of the present invention, the pharmacokinetic parameters are calculated as mean values taken from a population of individuals participating in the study.

The extended release liquid compositions also provide the consistent in-vivo release which ensures steady and predictable guanfacine release with minimal inter and intra subject variation throughout the shelf life of the composition.

The in-vitro dissolution release profile of the extended release liquid compositions upon storage for at least seven days remains substantially similar to the initial in-vitro dissolution release profile obtained as soon as practicable after preparation of the extended release liquid compositions. Particularly, the in-vitro dissolution release profile of the extended release liquid compositions upon storage at room temperature for at least one month remains substantially similar to the initial in-vitro dissolution release profile obtained as soon as practicable after preparation of the extended release liquid compositions. More particularly, the in-vitro dissolution release profile of the extended release liquid compositions upon storage at room temperature for at least three months remains substantially similar to the initial in-vitro dissolution release profile obtained as soon as practicable after preparation of the extended release liquid compositions. The in-vitro dissolution release profile is measured by using any known dissolution methods, in particular the in-vitro dissolution release is measured at 37° C. using a USP type II apparatus at 75 rpm, in 900 mL of hydrochloric acid buffer with a pH 2.2.

Guanfacine, particularly guanfacine hydrochloride, is found to degrade at high pH values. Solution state stability studies have indicated that at 16 hours, assay values of guanfacine have dropped down to 86.3% and 84% at pH 6.8 and 7.5 respectively and even further reduced at 24 hours. One of the major impurity of guanfacine is 2,6-dichlorophenyl acetic acid.

Inventors have surprisingly discovered that degradation of guanfacine can be prevented by maintaining the pH of the composition to less than about 6.8. In the present invention, the pH of the reconstituted liquid composition or ready-to-use liquid composition implies pH values measured for the pharmaceutically acceptable carrier, for the coated cores, or in the microenvironment of guanfacine, or combination of these that is sufficient to prevent degradation of guanfacine.

The term "stable," as used herein, refers to chemical stability, wherein the amount of impurity 2,6- dichlorophenyl acetic acid in the composition remains less than about 1.0% w/w, particularly less than about 0.7% w/w upon storage of the composition for a period of at least seven days, more particularly, for a period of at least one month, or further, to the extent necessary for the sale and use of the composition.

The extended release liquid composition is in the form of a ready-to-use liquid composition or a reconstituted liquid composition. The ready-to-use liquid composition comprises a suspension, a syrup, a concentrate, an elixir or an emulsion or like. The reconstituted liquid composition comprises a suspension reconstituted in the carrier from dry powder comprising pellets, granules, beads, or the like.

The present invention provides extended release liquid composition comprising:
(i) cores comprising guanfacine and a release-controlling agent; and
(ii) a pharmaceutically acceptable carrier.

The term "pharmaceutically acceptable carrier," as used herein, acts as a suspension base used to suspend the guanfacine cores. This pharmaceutically acceptable carrier comprises one or more of liquid adjuvants and other pharmaceutically acceptable excipients. When the composition is a reconstituted liquid composition, the powder for suspension comprising cores of guanfacine are reconstituted with the carrier comprising one or more of liquid adjuvants and other pharmaceutically acceptable excipients. Alternatively, one or more of other pharmaceutically acceptable excipients may be mixed with the cores of guanfacine which may then be reconstituted with a liquid adjuvant. The pharmaceutically acceptable carrier may be pre-formed or formed at the time of reconstitution.

The pharmaceutically acceptable carrier may play a role in creating a hypertonic environment. The term "hypertonic environment," as used herein, means that the pharmaceutically acceptable carrier has higher solute concentration which helps to generate high osmotic pressure such that there is no leaching of guanfacine from the extended release coated cores into the carrier.

The term "osmolality," as used herein, means the number of moles of any water-soluble compound per kg of the carrier. In the present invention, the osmolality may be measured according to known methods, such as using a Vapor pressure Osmometer, a Colloid Osmometer, or a Freezing Point Depression Osmometer such as Osmomat® 030-D or Osmomat® 3000, in particular by a Freezing Point Depression Osmometer. In the present invention, pharmaceutically acceptable carrier has an osmolality of about 1 osmol/kg or more than about 1 osmol/kg of the pharmaceutically acceptable carrier.

The term "osmolality ratio," as used herein, means the ratio of osmolality of the external phase to the osmolality of the internal phase. The external phase herein means the carrier without the coated cores of guanfacine. The internal phase herein means the coated cores of guanfacine.

As the direct measurement of the osmolality of the internal phase i.e., coated cores is difficult, the osmolality of the internal phase herein, is represented as the osmolality of a solution which prevents significant leaching of guanfacine from the coated cores into the solution. The leaching of guanfacine from the coated cores is determined by the difference in the osmolalities across the coating layer and the absence of any significant leaching from the coated cores directs that the osmolality of the solution has become equal to the osmolality of the coated cores. The osmolality ratio of the extended release liquid compositions of present invention is at least about 1.0.

The osmolality of the carrier remains equivalent upon storage for at least seven days. Particularly, the osmolality of the carrier measured after one month remains equivalent to the osmolality of the carrier measured as soon as practicable after preparation of the extended release liquid compositions. More particularly, the osmolality of the carrier measured after three months remains equivalent to the osmolality of the carrier measured as soon as practicable after preparation of the extended release suspension compositions. More particularly, the osmolality of the carrier measured after three months remains substantially similar to the osmolality of the carrier measured as soon as practicable after preparation of the extended release liquid compositions. The equivalent osmolality of the carrier ensures that there is no leaching of the guanfacine from the coated cores into carrier.

In certain embodiments, the pharmaceutically acceptable carrier in the present invention comprises one or more of liquid adjuvants and other pharmaceutically acceptable excipients.

Suitable liquid adjuvants comprise water. It may optionally comprise a co-solvent, for example, propylene glycol, glycerol, sorbitol, and the like, to assist solubilization and incorporation of various water-insoluble ingredients, such as flavoring oils and the like, into the composition.

In certain embodiments, other pharmaceutically acceptable excipients in the carrier are selected from the group comprising acids, osmogents, buffering agents, suspending agents, glidants, sweetening agents, flavors, colorants, anti-caking agents, wetting agents, preservatives, antioxidants, chelating agents, binders, viscosity modifiers, and combinations thereof.

Suitable acids are selected from the group comprising organic acids, inorganic acids or mixtures thereof. Organic acids are selected from the group comprising citric acid, fumaric acid, tartaric acid, oxalic acid, succinic acid, adipic acid, phthalic acid, acetic acid, alginic acid, ascorbic acid, aspartic acid, benzoic acid, cyclamic acid, erythorbic acid, glutamic acid hydrochloride, lactic acid, maleic acid, methacrylic acid, oleic acid, palmitic acid, sorbic acid, stearic acid, and combinations thereof. Inorganic acids are selected from the group comprising hydrochloric acid, hydrobromic acid, hydroiodic acid, nitric acid, phosphoric acid, sulfuric acid, boric acid, perchloric acid, and combinations thereof. Citric acid, fumaric acid, tartaric acid, ascorbic acid, benzoic acid, and hydrochloric acid are preferably used.

As used herein, the term "osmogents," refers to all pharmaceutically acceptable inert water-soluble compounds that can imbibe or dissolve in water and/or aqueous biological fluids. Suitable examples of osmogents or pharmaceutically acceptable inert water-soluble compounds are selected from the group comprising carbohydrates such as xylitol, mannitol, sorbitol, arabinose, ribose, xylose, glucose, fructose, mannose, galactose, sucrose, maltose, lactose, dextrose and raffinose; water-soluble salts of inorganic acids such as magnesium chloride, magnesium sulfate, potassium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, potassium dihydrogen phosphate, and sodium phosphate tribasic; water-soluble salts of organic acids such as sodium acetate, potassium acetate, magnesium succinate, sodium benzoate, sodium citrate, and sodium ascorbate; water-soluble amino acids such as glycine, leucine, alanine, methionine; urea or its derivatives; propylene glycol; glycerin; polyethylene oxide, xanthan gum, hydroxypropylmethyl cellulose; and mixtures thereof. Particularly, the osmogents used in the present invention are xylitol, mannitol, glucose, lactose, sucrose, and sodium chloride.

Suitable buffering agents are selected from the group comprising hydrochloric acid, citric acid, sodium citrate, potassium citrate, acetate, sodium acetate trihydrate, potassium dihydrogen orthophosphate, trisodium hydrogen orthophosphate, sodium dihydrogen orthophosphate, disodium hydrogen orthophosphate, and mixtures thereof.

Suitable suspending agents are selected from the group comprising cellulose derivatives such as co-processed spray dried forms of microcrystalline cellulose and carboxymethyl cellulose sodium, hydroxypropyl cellulose, hydroxyethyl cellulose, hydroxypropylmethyl cellulose, methylcellulose, carboxymethyl cellulose and its salts/derivatives, and microcrystalline cellulose; carbomers; gums such as locust bean gum, xanthan gum, tragacanth gum, arabinogalactan gum, agar gum, gellan gum, guar gum, apricot gum, karaya gum, sterculia gum, acacia gum, gum arabic, and carrageenan; pectin; dextran; gelatin; polyethylene glycols; polyvinyl compounds such as polyvinyl acetate, polyvinyl alcohol, and polyvinyl pyrrolidone; sugar alcohols such as xylitol and mannitol; colloidal silica; and mixtures thereof. The co-processed spray dried forms of microcrystalline cellulose and carboxymethyl cellulose sodium are marketed under the trade names Avicel® RC-501, Avicel® RC-581, Avicel® RC-591, and Avicel®CL-611.

Suitable glidants are selected from the group comprising silica, calcium silicate, magnesium silicate, colloidal silicon dioxide, corn starch, talc, stearic acid, magnesium stearate, calcium stearate, sodium stearyl fumarate, hydrogenated vegetable, and mixtures thereof.

Suitable sweetening agents are selected from the group comprising saccharine or its salts such as sodium, potassium, or calcium, cyclamate or its salt, aspartame, alitame, acesulfame or its salt, stevioside, glycyrrhizin or its derivatives, sucralose, and mixtures thereof.

Suitable flavors are selected from the group comprising peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloe vera balsam, spearmint, eucalyptus, and combinations thereof.

Suitable coloring agents are selected from the group comprising dyes, natural coloring agents or pigments, approved for use under Federal Food, Drug and Cosmetic Act.

Suitable anti-caking agents are selected from the group comprising colloidal silicon dioxide, tribasic calcium phosphate, powdered cellulose, magnesium trisilicate, starch, and mixtures thereof.

Suitable wetting agents are selected from the group comprising anionic, cationic, nonionic, or zwitterionic surfactants, and combinations thereof. Suitable examples of wetting agents are sodium lauryl sulphate; cetrimide; polyethylene glycols; polyoxyethylene-polyoxypropylene block copolymers such as poloxamers; polyglycerin fatty acid esters such as decaglyceryl monolaurate and decaglyceryl monomyristate; sorbitan fatty acid esters such as sorbitan monostearate; polyoxyethylene sorbitan fatty acid ester such as polyoxyethylene sorbitan monooleate; polyethylene glycol fatty acid ester such as polyoxyethylene monostearate; polyoxyethylene alkyl ether such as polyoxyethylene lauryl ether; polyoxyethylene castor oil; and mixtures thereof.

Suitable preservatives are selected from the group comprising parabens such as methyl, ethyl, propyl, and butyl p-hydroxybenzoic acid esters, alkyl hydroxybenzoates, sorbic acid or a salt thereof, benzoic acid or a salt thereof, salts of edetate (also known as salts of ethylenediaminetetraacetic acid or EDTA, such as disodium edetate), benzalkonium chloride, and mixtures thereof.

Suitable antioxidants are selected from the group comprising butylated hydroxytoluene (BHT), butylated hydroxyanisole (BHA), sodium metabisulfite, ascorbic acid, propyl gallate, thiourea, tocopherols, beta-carotene, and mixtures thereof.

Suitable chelating agents are selected from the group comprising ethylenediamine tetraacetic acid (EDTA) and its salts, such as, for example, dipotassium ethylenediamine tetraacetate, calcium disodium ethylenediamine tetraacetate, tetrasodium ethylenediamine tetraacetate, and mixtures thereof.

Suitable binders are selected from the group comprising polyvinyl pyrrolidone, starch, pregelatinized starch, hydroxypropylmethyl cellulose, hydroxyethyl cellulose, methyl cellulose, sodium carboxymethyl cellulose, gums, acrylate polymers, and mixtures thereof.

Suitable viscosity modifiers are selected from the group comprising chitosan, acacia, alginic acid bentonite, carbomers, carboxymethylcellulose calcium or sodium, cetostearyl alcohol, methyl cellulose, ethylcellulose, glycerin, gelatin guar gum, hydroxyethyl cellulose, hydroxymethyl cellulose, hydroxypropyl cellulose, hydroxypropyl methyl cellulose, any other suitable cellulose-based component, maltodextrin, polyvinyl alcohol, povidone, propylene carbonate, propylene glycol alginate, sodium alginate, starch, sodium starch glycolate, starch tragacanth, and xanthan gum, and mixtures thereof.

The extended release liquid composition may additionally include an immediate release component of guanfacine that can help in providing a biphasic or pulsatile type release. Immediate release component may help in providing an immediate therapeutic effect which could be subsequently followed by an extended therapeutic effect over a longer duration of time. The immediate release guanfacine may be present in the carrier in an amount that is less than the saturation amount. Alternatively, the amount of immediate release guanfacine may be more than the amount needed to form the saturated solution either initially or during storage of the extended release composition.

This immediate release component may be present in the form of powder, pellets, beads, spheroids or granules of guanfacine. Alternatively, the immediate release component may be present in the form of an immediate release coating of guanfacine over the extended release cores of guanfacine. Alternatively, the immediate release component of guanfacine may be present in form of guanfacine-resin complexes.

Cation- and anion-exchange resins are well-known in the art. Few exemplary resins that can be used according to the invention include, but are not limited to, Dowex® resins and others made by Dow Chemical; Amberlite®, Amberlyst® and other resins made by Rohm and Haas; Indion® resins made by Ion Exchange, Ltd. (India), Diaion® resins by Mitsubishi; Type AG® and other resins by BioRad; Sephadex® and Sepharose® made by Amersham; resins by Lewatit, sold by Fluka; Toyopearl® resins by Toyo Soda; IONAC® and Whatman® resins sold by VWR; and BakerBond® resins sold by J T Baker; hydrophilic colloids such as, e.g., alginate, chitsoan, carboxymethylcellulose, croscarmellose, microcrystalline cellulose, xanthan gum, carboxy vinyl polymers such as carbomer 94, polylysine, gelatin; and resins having polymer backbones comprising styrene-divinyl benzene copolymers and having pendant ammonium or tetraalkyl ammonium functional groups, available from Rohm and Haas, and sold under the tradename DUOLITE™ AP143; or any combinations thereof.

The viscosity of the pharmaceutically acceptable carrier ranges from about 300 cps to about 15,000 cps. Preferably, the viscosity of the carrier ranges from about 500 cps to about 10,000 cps. More preferably, the viscosity of the carrier ranges from about 500 cps to about 7,000 cps. The viscosity of the carrier of the present invention is measured by using a Brookfield Viscometer having a # 3 spindle rotating at 20 rpm at 25° C.

The cores may comprise guanfacine in the form of powder, granules, and pellets. Alternatively, guanfacine may be layered over an inert particle to form a core.

Alternatively, guanfacine may be in the form of complex with a suitable complexing agent such as cyclodextrin or ion-exchange resins.

The core is in the form of a bead, a pellet, a granule, a spheroid, or the like.

The term "inert particle," as used herein, refers to a particle made from a sugar sphere also known as a nonpareil seed, a microcrystalline cellulose sphere, a dibasic calcium phosphate bead, a mannitol bead, a silica bead, a tartaric acid pellet, a wax based pellet, and the like.

Release-controlling agent may be mixed with guanfacine in the core. Alternatively, release-controlling agent may be coated over the guanfacine core. Alternatively, release-controlling agent may be present both in the core and as coating over guanfacine cores.

The release-controlling agent present in the core and/or as coating over the core, is selected from the group comprising a pH-dependent release-controlling agent, a pH-independent release-controlling agent, or mixtures thereof.

Suitable examples of pH-dependent release-controlling agents are selected from the group comprising acrylic copolymers such as methacrylic acid and methyl methacrylate copolymers, e.g., Eudragit® L 100 and Eudragit® S 100, methacrylic acid and ethyl acrylate copolymers, e.g., Eudragit® L 100-55 and Eudragit® L 30 D-55, dimethyl-aminoethyl methacrylate and butyl methacrylate and methyl methacrylate copolymers e.g., Eudragit® E 100, Eudragit® E PO, methyl acrylate and methacrylic acid and octyl acrylate copolymers, styrene and acrylic acid copolymers, butyl acrylate and styrene and acrylic acid copolymers, and ethylacrylate-methacrylic acid copolymer; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

Suitable examples of pH-independent release-controlling agents are selected from the group comprising cellulosic polymers such as ethyl cellulose, methyl cellulose, hydroxyethyl cellulose, hydroxypropyl cellulose, hydroxyethylmethyl cellulose, hydroxypropylmethyl cellulose, cellulose acetate, and carboxy methylcellulose; acrylic copolymers such as methacrylic acid copolymers, e.g., Eudragit® RS, Eudragit® RL, Eudragit® NE 30 D; polyethylene derivatives e.g., polyethylene glycol and polyethylene oxide; polyvinyl alcohol; polyvinyl acetate; gums e.g., guar gum, locust bean gum, tragacanth, carrageenan, alginic acid, gum acacia, gum arabic, gellan gum, and xanthan gum; triglycerides; waxes, e.g., Compritol®, Lubritab®, and Gelucires®; lipids; fatty acids or their salts/derivatives; polyvinyl polymers; a mixture of polyvinyl acetate and polyvinyl pyrrolidone, e.g., Kollidon® SR; and mixtures thereof. In particular, the pH-independent polymer used in the present invention is ethyl cellulose.

The cores of the present invention may additionally comprise one or more of other pharmaceutically acceptable excipients selected from the group comprising acids, osmogents, binders, glidants, or combinations thereof. These have been defined above in the specification.

The diameter of the cores comprising guanfacine and a release-controlling agent has a $d_{90}$ value of less than about 1.5 mm. More particularly, the $d_{90}$ value is less than about 1.2 mm. It is desirable to keep the diameter of the cores within the specified size so as to avoid sedimentation of the cores, grittiness in the mouth and thereby rendering the composition more acceptable. The diameter of the cores is measured according to known methods, such as using Camsizer®.

As used herein, the term "$d_{90}$ value," means at least 90% of the cores have volume diameter in the specified range when measured by a suitable method, for example, Camsizer®.

The coating additives used in the present invention are selected from the group comprising plasticizers, opacifiers, anti-tacking agents, coloring agents, or combinations thereof.

Suitable plasticizers are selected from the group comprising triethyl citrate, dibutylsebacate, triacetin, acetylated triacetin, tributyl citrate, glyceryl tributyrate, diacetylated monoglyceride, rapeseed oil, olive oil, sesame oil, acetyl tributyl citrate, acetyl triethyl citrate, glycerin, sorbitol, diethyl oxalate, diethyl phthalate, diethyl malate, diethyl fumarate, dibutyl succinate, diethyl malonate, dioctyl phthalate, and mixtures thereof.

Suitable opacifiers are selected from the group comprising titanium dioxide, manganese dioxide, iron oxide, silicon dioxide, and combinations thereof.

Suitable anti-tacking agents are selected from the group comprising talc, magnesium stearate, calcium stearate, stearic acid, silica, glyceryl monostearate, and mixtures thereof.

Suitable coloring agents are selected from the group consisting of FD&C (Federal Food, Drug and Cosmetic Act) approved coloring agents; natural coloring agents; natural juice concentrates; pigments such as iron oxide, titanium dioxide, and zinc oxide; and mixtures thereof.

Suitable solvents used for granulation or for forming a solution or dispersion for coating are selected from the group comprising water, ethanol, methylene chloride, isopropyl alcohol, acetone, methanol, and combinations thereof.

The term "about," as used herein, refers to any value which lies within the range defined by a variation of up to ±10% of the value.

The term "equivalent," as used herein, refers to any value which lies within the range defined by a variation of up to ±30% of the value.

The term "significant leaching," as used herein, means more than 20% of the guanfacine is leached out from the coated cores into the carrier.

The extended release liquid compositions of the present invention are homogenous and delivers the desired dose of guanfacine in every use without any risk of overdosing or under dosing.

The amounts of each excipient can readily be determined or ascertained by the person skilled in the art.

The invention also provides for methods of making the compositions described herein by usual methods well known in the art.

The cores of the present invention comprising guanfacine can be prepared by any method known in the art, e.g., extrusion-spheronization, wet granulation, dry granulation, hot-melt extrusion granulation, spray drying, and spray congealing. Alternatively, guanfacine can be layered over an inert particle to form the core by conventional coating processes.

Further, guanfacine can be directly coated with a release-controlling agent to form the microparticles or microcapsules. The microparticles or microcapsules can be prepared by a process of homogenization, solvent evaporation, coacervation, phase separation, spray drying, spray congealing, polymer precipitation, or supercritical fluid extraction.

Coating may be performed by applying the coating composition as a solution/suspension/ blend using any conventional coating technique known in the art, such as spray coating in a conventional coating pan, fluidized bed processor, dip coating, or compression coating. The percentage of the coating build-up shall be varied depending on the required extended release.

The process also includes forming complexes of guanfacine with ion-exchange resins, comprising loading a plurality of resin particles with guanfacine to form drug-resin particles. These particles may optionally be further coated with immediate release or extended release coating using conventional techniques. Methods of loading drugs onto resin particles are generally known in the art.

The ready-to-use extended release liquid compositions of the present invention may be packaged in a suitable package such as a bottle. The dry powder for reconstitution may be packaged in a suitable package such as a bottle or a sachet. Further, the sachet can be filled as a unit dose or a multi dose sachet. The present invention further includes a co-package or a kit comprising two components, wherein one package or one component comprises a dry powder and another package or another component comprises the pharmaceutically acceptable carrier. Alternatively, a twin chamber pack with two chambers can be used. In this case, one chamber comprises a powder for suspension and another chamber comprises the carrier.

The invention also provides for various methods of treatment using the compositions described herein. In a particular embodiment, the invention provides for methods of treating ADHD comprising administering an effective amount of any of the composition described herein.

The invention may be further illustrated by the following examples, which are for illustrative purposes only and should not be construed as limiting the scope of the invention in any way.

TABLE 1 pH dependent degradation profile (Guanfacine hydrochloride)-solution state stability

| Time (hours) | % Assay | | | | |
|---|---|---|---|---|---|
| | pH 1.2 | pH 2.2 | pH 4.5 | pH 6.8 | pH 7.5 |
| 0 | 101.2 | 100.3 | 99.4 | 99.5 | 100.9 |
| 1 | 101.2 | 100.5 | 99.0 | 99.0 | 99.9 |
| 4 | 101.2 | 100.4 | 98.7 | 97.2 | 97.1 |
| 8 | 101.1 | 100.4 | 98.9 | 93.7 | 92.2 |
| 16 | 101.6 | 100.3 | 98.7 | 86.3 | 84.0 |
| 24 | 101.4 | 100.2 | 98.5 | 79.9 | 77.5 |

As can be seen from the above Table 1, the assay values of guanfacine are substantially decreasing over time at high pH values, clearly indicating decreased stability of guanfacine at high pH. On the other hand, no major changes in assay values of guanfacine were observed in acidic conditions over time, indicating guanfacine is stable at lower pH values.

EXAMPLES 1-2

Comparative Compositions of Guanfacine

| | Quantity/unit (in mg) | |
|---|---|---|
| Ingredients | Example 1 | Example 2-Comparative Example |
| Guanfacine hydrochloride | 1.15 | 1.15 |
| Citric acid | 1.40 | 0.00 |
| Xylitol | 690.00 | 690.00 |
| Water | q.s. to 1 mL | q.s. to 1 mL |

Procedure:
Guanfacine hydrochloride, xylitol, citric acid (in Example 1) were mixed in water to form liquid compositions.

Stability Studies

The compositions prepared as per Example 1 and Example 2 (Comparative Example) were stored at room temperature and the samples were analyzed after 3 days and 7 days. Stability results are represented in Table 2 below.

TABLE 2

Stability data of compositions prepared as per Example 1 and Example 2

| Impurities/Related substances (RS) (% w/w) | ICH Specification | Example 1 | Example 2-Comparative Example |
|---|---|---|---|
| | | 3 days- Room temperature | |
| 2,6-Dichlorophenylacetic acid | NMT 0.7 | 0.02 | 0.13 |
| Highest Unknown Impurity | NMT 0.5 | 0.00 | 0.87 |
| Total RS | NMT 2.0 | 0.02 | 1.76 |
| | | 7 days- Room temperature | |
| 2,6-Dichlorophenylacetic acid | NMT 0.7 | 0.06 | 0.14 |
| Highest Unknown Impurity | NMT 0.5 | 0.03 | 0.87 |
| Total RS | NMT 2.0 | 0.11 | 1.24 |

As seen from the above Table 2, it is observed that the amounts of impurity 2,6-dichlorophenyl acetic acid and total related substances was significantly reduced in composition having an acid as compared to the composition without an acid. Hence, it is clear that inclusion of an acid enhanced the stability of guanfacine.

EXAMPLES 3-5

Compositions of Guanfacine With Different Acids

| | Quantity/unit (in mg) | | |
|---|---|---|---|
| Ingredients | Example 3 | Example 4 | Example 5 |
| Guanfacine hydrochloride | 1.15 | 1.1.5 | 1.15 |
| Fumaric acid | 3.5 | — | — |
| Tartaric acid | — | 3.5 | — |
| Citric acid | — | — | 3.5 |
| Water | q.s. to 1 mL | q.s. to 1 mL | q.s. to 1 mL |

Procedure:
Guanfacine hydrochloride, suitable acid (fumaric/tartaric/citric acids) were mixed in water to form liquid compositions.

Stability Studies

The compositions prepared as per Examples 3-5 were stored at room temperature and the samples were analyzed after 30 days. Stability results are represented in Table 3 below.

TABLE 3

Stability data of compositions prepared as per Examples 3-5

| Impurities/Related substances (RS) (% w/w) | ICH Specification | Example 3 | Example 4 | Example 5 |
|---|---|---|---|---|
| | | 30 days- Room temperature | | |
| 2,6-Dichlorophenylacetic acid | NMT 0.7 | 0.23 | 0.22 | 0.27 |
| Highest Unknown Impurity | NMT 0.5 | 0.05 | 0.04 | 0.04 |
| Total RS | NMT 2.0 | 0.31 | 0.28 | 0.32 |

As seen from the above Table 3, equivalent stability results have been obtained with all the three studied acids i.e. fumaric acid, tartaric acid and citric acid.

EXAMPLES 6-8

Guanfacine Extended Release Powder for Suspension Compositions

| | Quantity/unit (in mg) | | |
|---|---|---|---|
| Ingredients | Example 6 | Example 7 | Example 8 |
| Drug layered core | | | |
| Microcrystalline cellulose spheres | 30.00 | 30.00 | 30.00 |
| Guanfacine hydrochloride | 1.15 | 1.15 | 1.15 |
| Hydroxypropylmethyl cellulose | 4.00 | 4.00 | 4.00 |
| Citric acid | 0.02 | 0.2 | 0.50 |
| Mannitol | 3.00 | 3.00 | 3.00 |
| Purified water | q.s. | q.s. | q.s. |
| Extended release (ER) coated core | 35% w/w coating | 35% w/w coating | 44.26% w/w coating |
| Ethyl cellulose | 12.02 | 12.08 | 15.40 |
| Dibutyl sebacate | 1.33 | 1.34 | 1.71 |
| Acetone | q.s. | q.s. | q.s. |
| Purified water | q.s. | q.s. | q.s. |
| Weight of ER coated core | 51.52 | 51.77 | 55.76 |
| Carrier composition | | | |
| Microcrystalline cellulose - sodium carboxymethyl cellulose (Avicel ®CL-611) | 20.00 | 20.00 | 20.00 |
| Xanthan gum | 1.50 | 1.50 | 1.50 |
| Colloidal silicon dioxide | 3.50 | 3.50 | 3.50 |
| Sucralose | 0.50 | 0.50 | 0.50 |
| Xylitol | 450.00 | 450.00 | 450.00 |
| Strawberry flavor | 2.00 | 2.00 | 2.00 |
| Citric acid | 1.40 | 1.40 | 1.40 |
| Methyl paraben | — | 1.80 | 1.80 |
| Propyl paraben | — | 0.20 | 0.20 |
| Purified water | q.s. to 1 mL | q.s. to 1 mL | q.s. to 1 mL |

Procedure:
1. Citric acid, mannitol, hydroxypropylmethyl cellulose, guanfacine hydrochloride were dissolved in purified water.
2. Microcrystalline cellulose spheres were coated with the solution of step 1.
3. Ethyl cellulose and dibutyl sebacate were dispersed in a mixture of acetone and purified water.
4. The drug layered cores of step 2 were coated with the coating dispersion of step 3 to form extended release powder for suspension.
5. Microcrystalline cellulose-sodium carboxymethyl cellulose, xanthan gum, colloidal silicon dioxide, sucralose, xylitol, strawberry flavor, citric acid, methyl/propyl paraben (if present) were mixed in purified water to form the pharmaceutically acceptable carrier.
6. The extended release powder for suspension and the pharmaceutically acceptable carrier were separately packed in a twin chamber pack.

Stability Studies

The extended release powder for suspension compositions prepared as per Examples 7 and 8 were stored at 40° C./75% RH for 3 months and 1 month respectively. Thereafter, the powder for suspension was reconstituted with the carrier and the amounts of impurity 2,6-dichlorophenyl acetic acid and total related substances was determined. The initial levels of impurities/related substances and levels after 3 months/1 month are represented in Table 4 below.

TABLE 4

Stability data of the reconstituted liquid compositions prepared as per Examples 7-8

| | | Example 7 | | Example 8 | |
|---|---|---|---|---|---|
| Impurities/Related substances (RS) (% w/w) | ICH Specification | Initial | 40° C./ 75% RH - 3M | Initial | 40° C./ 75% RH - 1M |
| 2-6 Dichlorophenyl acetic acid | NMT 0.7 | 0.03 | 0.22 | 0.00 | 0.06 |
| Highest Unknown | NMT 0.5 | 0.05 | 0.03 | 0.03 | 0.02 |
| Total RS | NMT 2.0 | 0.14 | 0.34 | 0.03 | 0.08 |

In-Vitro Studies

The extended release powder for suspension prepared as per Examples 6 and 8 was reconstituted with the carrier and the in-vitro dissolution was determined for 4 mg dose at day 0 using USP type II apparatus at 75 rpm, in 900 mL of hydrochloric acid buffer with pH 2.2 at 37° C. The results of the release studies are represented in Table 5.

TABLE 5

Percentage (%) of guanfacine release from reconstituted compositions prepared as per Examples 6 and 8 in 900 mL hydrochloric acid buffer pH 2.2, USP type II, 75 rpm

| | Percentage (%) of guanfacine release | |
|---|---|---|
| Time (hours) | Example 6 | Example 8 |
| 1 | 18 | 11 |
| 2 | 38 | 29 |
| 4 | 58 | 54 |
| 6 | 68 | 68 |
| 12 | 79 | 83 |
| 16 | 83 | 87 |
| 20 | — | 90 |
| 24 | — | 92 |

EXAMPLES 9-12

Guanfacine Extended Release Powder for Suspension Compositions

| | Quantity/unit (in mg) | | | |
|---|---|---|---|---|
| Ingredients | Example 9 | Example 10 | Example 11 | Example 12 |
| Drug layered core | | | | |
| Microcrystalline cellulose spheres | 30.00 | 30.00 | 30.00 | 30.00 |

-continued

| Ingredients | Example 9 | Example 10 | Example 11 | Example 12 |
|---|---|---|---|---|
| Guanfacine hydrochloride | 1.15 | 1.15 | 1.15 | 1.15 |
| Hydroxypropylmethyl cellulose | 4.00 | 4.00 | 4.00 | 4.00 |
| Citric acid | 0.50 | 0.50 | 0.50 | 0.50 |
| Mannitol | 3.00 | 3.00 | 3.00 | 3.00 |
| Purified water | q.s. | q.s. | q.s. | q.s. |
| Extended release (ER) coated core | | 44.26% w/w coating | | |
| Ethyl cellulose | 15.4 | 15.4 | 15.4 | 15.4 |
| Dibutyl sebacate | 1.71 | 1.71 | 1.71 | 1.71 |
| Acetone | q.s. | q.s. | q.s. | q.s. |
| Purified water | q.s. | q.s. | q.s. | q.s. |
| Weight of ER coated core | 55.76 | 55.76 | 55.76 | 55.76 |
| Carrier composition | | | | |
| Xylitol | 690.00 | 300.00 | 495.00 | 690.0 |
| Citric acid | 0.50 | 5.00 | 2.75 | 5.00 |
| Purified water | q.s. to 1 mL | q.s. to 1 mL | q.s. to 1 mL | q.s. to 1 mL |

Procedure:
1. Citric acid, mannitol, hydroxypropylmethyl cellulose, guanfacine hydrochloride were dissolved in purified water.
2. Microcrystalline cellulose spheres were coated with the solution of step 1.
3. Ethyl cellulose and dibutyl sebacate were dispersed in a mixture of acetone and purified water.
4. The drug layered cores of step 2 were coated with the coating dispersion of step 3 to form extended release powder for suspension.
5. Xylitol and citric acid were mixed in purified water to form the pharmaceutically acceptable carrier.
6. The extended release powder for suspension was reconstituted with the pharmaceutically acceptable carrier and packed in a suitable container.

Stability Studies

The compositions prepared as per Examples 9-12 were stored at room temperature for 30 days. After 30 days, the amounts of impurity 2,6-dichlorophenyl acetic acid and total related substances was determined. The results are represented in Table 6 below.

TABLE 6

Stability data of the reconstituted liquid compositions prepared as per Examples 9-12

| Impurities/Related substances (RS) (% w/w) | ICH Specification | Example 9 | Example 10 | Example 11 | Example 12 |
|---|---|---|---|---|---|
| | | 30 days- Room Temperature | | | |
| 2,6-Dichlorophenylacetic acid | NMT 0.7 | 0.11 | 0.13 | 0.12 | 0.09 |
| Highest Unknown | NMT 0.5 | 0.05 | 0.05 | 0.05 | 0.04 |
| Total RS | NMT 2.0 | 0.16 | 0.18 | 0.17 | 0.13 |

In-Vitro Studies

The powder for suspension compositions prepared as per Examples 9-11 was stored for 10 days/30 days. After 10 days/30 days, the in-vitro dissolution was determined for 4 mg dose using USP type II apparatus at 75 rpm, in 900 mL of hydrochloric acid buffer with pH 2.2 at 37° C. The results of the release studies are represented in Table 7 below.

TABLE 7

Percentage (%) of guanfacine release from reconstituted liquid compositions prepared as per Examples 9-11 in hydrochloric acid buffer pH 2.2, USP type II, 75 rpm, 900 ml

| | Percentage (%) of Guanfacine Release | | | | | |
|---|---|---|---|---|---|---|
| | Example 9 | | Example 10 | | Example 11 | |
| Time (hours) | 10 days | 30 days | 10 days | 30 days | 10 days | 30 days |
| 1 | 12 | 14 | 25 | 27 | 18 | 21 |
| 2 | 29 | 31 | 37 | 39 | 33 | 35 |
| 4 | 51 | 52 | 55 | 56 | 54 | 55 |
| 6 | 65 | 65 | 67 | 68 | 67 | 67 |
| 12 | 83 | 82 | 83 | 83 | 84 | 83 |
| 16 | 88 | 87 | 88 | 88 | 88 | 87 |
| 20 | 90 | 90 | 90 | 91 | 91 | 90 |
| 24 | — | 92 | — | 93 | — | 92 |

EXAMPLES 13-14

Guanfacine Extended Release Powder for Suspension Compositions

| Ingredients | Example 13 | Example 14 |
|---|---|---|
| Drug Layered core | | |
| Microcrystalline cellulose spheres | 30.00 | 30.00 |
| Guanfacine hydrochloride | 1.15 | 1.15 |
| Hydroxypropylmethyl cellulose | 4.00 | 4.00 |
| Citric acid | 0.50 | 0.50 |
| Mannitol | 2.00 | 2.00 |
| Purified water | q.s. | q.s. |
| Extended release (ER) coated core | 50% w/w coating | 42.86% w/w coating |
| Ethyl cellulose | 16.94 | 14.52 |
| Dibutyl sebacate | 1.88 | 1.61 |
| Acetone | q.s. | q.s. |
| Purified water | q.s. | q.s. |
| Weight of ER coated core | 56.47 | 53.78 |
| Carrier composition | | |
| Microcrystalline cellulose - sodium carboxymethyl cellulose (Avicel ® CL-611) | 20.00 | 20.00 |
| Xanthan gum | 2.50 | 1.50 |
| Colloidal silicon dioxide | 3.50 | 3.50 |
| Sucralose | 0.50 | 0.50 |
| Xylitol | 550.00 | 550.00 |
| Strawberry flavor | 2.00 | 2.00 |
| Citric acid | 1.40 | 1.40 |
| Methyl paraben | 1.80 | 1.80 |
| Propyl paraben | 0.20 | 0.20 |
| Purified water | q.s. to 1 mL | q.s. to 1 mL |

Procedure:
1. Citric acid, mannitol, hydroxypropyl methylcellulose, guanfacine hydrochloride were dissolved in purified water.
2. Microcrystalline cellulose spheres were coated with the solution of step 1.
3. Ethyl cellulose and dibutyl sebacate were dispersed in a mixture of acetone and purified water.

4. The drug layered cores of step 2 were coated with the coating dispersion of step 3 to form extended release powder for suspension.
5. Microcrystalline cellulose-sodium carboxymethyl cellulose, xylitol, citric acid, xanthan gum, colloidal silicon dioxide, sucralose, strawberry flavor, methyl paraben and propyl paraben were mixed in purified water to form the pharmaceutically acceptable carrier.
6. The extended release powder for suspension and the pharmaceutically acceptable carrier were separately packed in a twin chamber pack.

Stability Studies

The extended release powder for suspension composition prepared as per Example 14 was stored at 40° C./75% RH for one month. After one month, the powder for suspension was reconstituted with the carrier and the amounts of impurity 2,6-dichlorophenyl acetic acid and total related substances was determined. The initial levels of impurities/related substances and levels after 1 month are represented in Table 8 below.

TABLE 8

Stability data of reconstituted liquid compositions prepared as per Example 14

| Impurities/ | | Example 14 | |
|---|---|---|---|
| Related substances (RS) (% w/w) | ICH Specification | Initial | 40° C./ 75% RH - 1 M |
| 2-6 Dichlorophenyl acetic acid | NMT 0.7 | 0.01 | 0.10 |
| Highest Unknown | NMT 0.5 | 0.03 | 0.03 |
| Total RS | NMT 2.0 | 0.10 | 0.16 |

In-Vitro Studies

The extended release powder for suspension prepared as per Example 14 was stored at 40° C./75% RH for one month. After one month, the in-vitro dissolution was determined for 4 mg dose using USP type II apparatus at 75 rpm, in 900 mL of hydrochloric acid buffer with pH 2.2 at 37° C. The results of the initial release studies and after 1 month are represented in Table 9 below.

TABLE 9

Percentage (%) of guanfacine release from extended release powder for suspension prepared as per Example 14 in 900 mL of hydrochloric acid buffer, pH 2.2, USP type II, 75 rpm

| | Percentage (%) of guanfacine release | |
|---|---|---|
| Time (hours) | Initial | 40° C./75% RH - 1 M |
| 1 | 19 | 22 |
| 2 | 33 | 36 |
| 4 | 46 | 50 |
| 6 | 55 | 59 |
| 12 | 68 | 74 |
| 16 | 73 | 79 |
| 20 | 76 | 82 |
| 24 | 79 | 84 |

Core Size Measurements

The sizes of the guanfacine layered cores and the extended release coated cores prepared as per Example 14 were measured by Camsizer and the results are provided in Table 10 below:

TABLE 10

Core sizes

| Sample | Core sizes |
|---|---|
| Guanfacine layered core (without ER coating) | $d_{90}$ = 0.255 mm $d_{50}$ = 0.187 mm $d_{10}$ = 0.141 mm |
| Extended release coated core | $d_{90}$ = 0.349 mm $d_{50}$ = 0.239 mm $d_{10}$ = 0.181 mm |

Viscosity Measurements

Viscosity of the carrier prepared as per Example 14 was measured by Brookfield viscometer. The values are provided in the Table 11 below.

TABLE 11

Viscosity measurements

| Sample | Results |
|---|---|
| Viscosity of the carrier as per Example 14 | Spindle 3 rpm = 20 % torque = 18.1%, Viscosity = 905 cps |

Osmolality Measurements

Osmolality measurements for composition prepared as per Example 13 were carried out using Osmomat 30D. Results are presented in the Table 12 below:

TABLE 12

Osmolality measurements

| Name of Sample | Osmolality (OSMOL/Kg) |
|---|---|
| Guanfacine hydrochloride (API) (1 mg/mL) | 0.006 |
| Carrier | 4.105 |
| ER pellet composition (1 mg/unit) + vehicle | 4.190 |
| Final ER PFOS composition (1 mg/mL) | 4.025 |

Osmolality Measurement of the External Phase

Xylitol, microcrystalline cellulose-sodium carboxymethyl cellulose, xanthan gum, strawberry flavor, sucralose, citric acid, methyl paraben, propyl paraben and colloidal silicon dioxide, purified water were mixed as per Example 13. This suspension was then filtered and diluted with purified water, and the osmolality of the external phase was measured using Osmomat 030-D.

Osmolality of the external phase/carrier was determined to be 4.105 osmol/kg of the carrier.

Osmolality Measurement of the Internal Phase

Various solutions having various concentrations of sodium chloride were prepared as per Examples (A)-(D). The osmolalities of these solutions were measured using Osmomat 030-D.

| Ingredient | Example A | Example B | Example C | Example D |
|---|---|---|---|---|
| Sodium Chloride (mg) | 30.00 | 60.00 | 120.00 | 180.00 |
| Purified water | q.s. to 1 mL | q.s. to 1 mL | q.s. to 1 mL | q.s. to 1 mL |
| Osmolality (osmol/kg) | 0.910 | 1.787 | 3.574* | 5.361* |

*Extrapolated using values of dilute solutions

Sodium chloride was dissolved in purified water as per Examples A-D. The osmolality of these solutions were measured using Osmomat 030-D.

TABLE 13

Extended release coated cores for osmolality measurements

| Ingredients | Quantity (mg) |
|---|---|
| Drug layered core | |
| Guanfacine hydrochloride | 1.15 |
| Microcrystalline cellulose spheres | 4.00 |
| Hydroxypropylmethyl cellulose | 30.00 |
| Mannitol | 10.00 |
| Purified Water | q.s. |
| Extended Release (ER) coated core | |
| Ethyl cellulose | 14.22 |
| Dibutyl sebacate | 1.58 |
| Acetone | q.s. |
| Purified Water | q.s. |
| Weight of Extended release (ER) coated core | 60.95 |

The coated cores for osmolality measurement of internal phase were prepared as provided in above Table 13. These cores were dispersed in different solutions as per Examples A-D. These suspensions were kept for seven days at room temperature. After seven days, each suspension was filtered and diluted with purified water. These were then analyzed by using HPLC for guanfacine content. The results are represented in Table 14.

TABLE 14

Effect of Osmolality on Guanfacine Leaching

| Example | Osmolality (Osmol/kg) of the solution | Guanfacine Content (%) |
|---|---|---|
| A | 0.910 | 69.80 |
| B | 1.787 | 8.90 |
| C | 3.574* | 1.30 |
| D | 5.361* | 0.30 |

*Extrapolated using values of dilute solutions

From the above data, it is evident that the leaching of guanfacine from the coated cores into the solution was decreasing as the osmolality of the solution was increasing from Examples A-D. The leaching is found to be significantly reduced from Example C onwards. The osmolality of the composition prepared according to Example C is considered to be osmolality of the internal phase.

Osmolality ratio is calculated to be 1.149.

EXAMPLE 15

Guanfacine Extended Release Powder for Suspension Compositions

| Ingredients | Quantity/unit (in mg) |
|---|---|
| Drug layered core | |
| Microcrystalline cellulose spheres | 30.00 |
| Guanfacine hydrochloride | 1.15 |
| Citric acid | 0.50 |
| Eudragit ®L 100-55 | 1.50 |
| Triethyl citrate | 0.15 |
| Talc | 0.45 |
| Acetone | q.s. |
| Purified water | q.s. |
| Extended release (ER) coated core | 15% w/w coating |
| Ethyl cellulose | 4.56 |
| Dibutyl sebacate | 0.51 |
| Acetone | q.s. |
| Purified water | q.s. |
| Weight of ER coated core | 38.82 |
| Carrier composition | |
| Microcrystalline cellulose - sodium carboxymethyl cellulose (Avicel ® CL-611) | 40.00 |
| Xanthan gum | 2.50 |
| Aerosil | 3.50 |
| Sucralose | 0.50 |
| Xylitol | 550.00 |
| Strawberry flavor | 2.00 |
| Citric acid | 1.40 |
| Methyl paraben | 1.80 |
| Propyl paraben | 0.20 |
| Purified water | q.s. to 1 mL |

Procedure:

1. Citric acid, Eudragit L 100-55, triethyl citrate, talc, guanfacine hydrochloride were dispersed in a mixture of acetone and purified water.
2. Microcrystalline cellulose spheres were coated with the dispersion of step 1.
3. Ethyl cellulose and dibutyl sebacate were dispersed in a mixture of acetone and purified water.
4. The drug layered cores of step 2 were coated with the coating dispersion of step 3 to form extended release powder for suspension.
5. Microcrystalline cellulose-sodium carboxymethyl cellulose, xylitol, citric acid, xanthan gum, colloidal silicon dioxide, sucralose, strawberry flavor, methyl paraben and propyl paraben were mixed in purified water to form the pharmaceutically acceptable carrier.
6. The extended release powder for suspension and the pharmaceutically acceptable carrier were separately packed in a twin chamber pack.

Bioequivalence Study of Guanfacine Extended Release Powder for Oral Suspension

The extended release liquid composition of Example 14 having a concentration of 1 mg/mL was dosed in an amount equivalent to 4 mg of guanfacine (Test product). This composition was compared with the commercially available extended release tablet composition of guanfacine (Intuniv® 4 mg tablets) (Reference product).

Fifteen healthy adult volunteers were enrolled for the study and fourteen completed at least two periods. An open label, balanced, randomized, three treatment, three-period, three sequence, relative bioavailability study was carried out under fasting condition. Blood samples were collected at appropriate time intervals and plasma concentrations of guanfacine were determined. The study was monitored in terms of $AUC_{0\rightarrow\infty}$, $AUC_{last}$, $C_{max}$, $T_{lag}$, $T_{max}$ achieved with the test product and reference product.

Tables 15 and 16 indicate the results of the study. It was observed that the extended release composition of the present invention is bioequivalent to marketed extended release tablet composition.

TABLE 15

Pharmacokinetic parameters of the composition prepared in Example 14 against reference product (Intuniv ®)

| Pharmacokinetic parameters | Composition of Example 14 (Test product) | Intuniv ® (Reference product) |
|---|---|---|
| $C_{max}$ (pg/mL) | 2738.85 | 3205.70 |
| $T_{max}$ (hr) | 5.00 | 5.50 |
| $T_{lag}$ (hr) | 0.07 | 0.00 |
| $AUC_{last}$ (hr * pg/mL) | 75035.51 | 79154.19 |
| $AUC_{0\to\infty}$ (hr * pg/mL) | 77178.70 | 81092.95 |

TABLE 16

Relative bioavailability in fasting condition (T/R)

| Pharmacokinetic Parameters | Ratio (%) | 90% C.I. | Intra Subject CV (%) |
|---|---|---|---|
| $C_{max}$ (ng/ml) | 88.32 | 77.51-100.65 | 19.70 |
| $AUC_{last}$ (ng · hr/mL) | 97.17 | 84.15-112.19 | 21.73 |
| $AUC_{0\to\infty}$ (ng · hr/mL) | 97.42 | 84.76-111.98 | 21.03 |

We claim:

1. A stable extended release suspension composition comprising guanfacine in an amount of 1 mg/ml comprising
   a) coated cores consisting of
      i. cores comprising guanfacine; and
      ii. coating comprising pH-independent release controlling agent over the cores of i;
   b) a pharmaceutically acceptable carrier
wherein the guanfacine is not present as guanfacine-resin complex and not more than about 30% of guanfacine is released from the composition after 1 hour when determined by a dissolution method using USP type II apparatus at 75 rpm, in 900 mL of hydrochloric acid buffer with a pH of 2.2 at 37° C.

2. The stable extended release suspension composition of claim 1, wherein the composition exhibits an area under the curve $(AUC)_{last}$ ranging from about 32000 hr*pg/mL to about 180000 hr*pg/mL upon administration of a 4 mg dose of guanfacine under fasting state.

3. The stable extended release suspension composition of claim 1, wherein the composition exhibits $C_{max}$ from about 1800 pg/mL to about 9000 pg/mL upon administration of a 4 mg dose of guanfacine under fasting state.

4. The stable extended release suspension composition of claim 1, wherein the composition exhibits $T_{max}$ from about 2 hours to about 10 hours, upon administration of a 4 mg dose of guanfacine under fasting state.

5. The stable extended release suspension composition of claim 1, wherein the composition exhibits $T_{lag}$ of less than about 2 hours, upon administration of a 4 mg dose of guanfacine under fasting state.

6. The stable extended release suspension composition of claim 1, wherein the composition is characterized by having an in-vitro dissolution release profile using USP type II apparatus at 75 rpm, in 900 mL of hydrochloric acid buffer with a pH of 2.2 at 37° C. as follows:
   i about 35% to about 75% of guanfacine released after 4 hours, and;
   ii not less than about 75% of guanfacine released after 24 hours.

7. The stable extended release suspension composition of claim 6, wherein the in-vitro dissolution release profile of the extended release liquid composition upon storage for at least seven days remains substantially similar to the initial in-vitro dissolution release profile.

8. The stable extended release suspension composition of claim 1, wherein the composition has a pH of less than about 6.8.

9. The stable extended release suspension composition of claim 1, wherein the composition is a ready-to-use liquid composition or a reconstituted liquid composition.

10. The stable extended release suspension composition of claim 1, wherein guanfacine may be present in the core or layered over an inert particle to form a core.

11. A stable extended release suspension composition of guanfacine in an amount of 1 mg/ml comprising
   a. coated cores consisting of:
      i. inert particles
      ii. drug layer comprising guanfacine over the inert particle to form a core; and
      iii. coating comprising pH-independent release controlling agent over cores of ii;
   b) a pharmaceutically acceptable carrier
wherein the guanfacine is not present as guanfacine-resin complex and not more than about 30% of guanfacine is released from the composition after 1 hour when determined by a dissolution method using USP type II apparatus at 75 rpm, in 900 mL of hydrochloric acid buffer with a pH of 2.2 at 37° C.

12. The stable extended release suspension composition of claim 11, wherein the composition comprises less than about 1.0% w/w of 2,6-dichlorophenyl acetic acid.

13. The stable extended release suspension composition of claim 11, wherein the composition comprises less than about 3.0% w/w of total related substances.

14. The stable extended release suspension composition of claim 11, wherein the core further comprises one or more pharmaceutically acceptable excipients selected from the group consisting of acids, osmogents, binders, glidants, and combinations thereof.

15. The stable extended release suspension composition of claim 11, wherein the carrier comprises one or more of liquid adjuvants and other pharmaceutically acceptable excipients.

16. The stable extended release suspension composition of claim 11, wherein the other pharmaceutically acceptable excipients in the carrier are selected from the group comprising acids, osmogents, buffering agents, suspending agents, glidants, sweetening agents, flavors, colorants, anti-caking agents, wetting agents, preservatives, antioxidants, chelating agents, binders, viscosity modifiers, and combinations thereof.

17. The stable extended release suspension of claim 11, wherein the composition is characterized by having an osmolality ratio of at least about 1.

18. The stable extended release suspension of claim 11, wherein the pharmaceutically acceptable carrier has an osmolality of about 1 osmol/kg or more than about 1 osmol/kg of the pharmaceutically acceptable carrier.

* * * * *